United States Patent [19]

Rector et al.

[11] Patent Number: 5,049,561
[45] Date of Patent: Sep. 17, 1991

[54] ANTHELMINTIC ACYLHYDRAZONES, METHOD OF USE AND COMPOSITIONS

[75] Inventors: Douglas L. Rector, Kalamazoo; George A. Conder, Richland; Sylvester D. Folz, Kalamazoo, all of Mich.

[73] Assignee: The Upjohn Company, Kalamazoo, Mich.

[21] Appl. No.: 455,321

[22] PCT Filed: Jul. 19, 1988

[86] PCT No.: PCT/US88/02367

§ 371 Date: Jan. 30, 1990

§ 102(e) Date: Jan. 30, 1990

Related U.S. Application Data

[63] Continuation-in-part of Ser. No. 80,522, Jul. 31, 1987, abandoned.

[51] Int. Cl.$^5$ ............... A61K 31/495; A61K 31/35; A61K 31/425; C07D 241/02
[52] U.S. Cl. ............... 514/252; 514/255; 514/365; 514/459; 544/336; 544/405; 544/408; 544/409; 544/410; 546/207; 546/209; 548/187; 549/426
[58] Field of Search ............ 544/405, 336, 408, 409, 544/410; 548/187; 549/426; 514/252, 255, 365, 459; 546/207, 209

[56] References Cited

U.S. PATENT DOCUMENTS 4,870,082 9/1989 Rector et al. ............... 514/311

FOREIGN PATENT DOCUMENTS 1479239 7/1977 United Kingdom .

WO86/04582 8/1986 World Int. Prop. O. .
WO86/05982 10/1986 World Int. Prop. O. .
WO87/06127 10/1987 World Int. Prop. O. .
WO87/06132 10/1987 World Int. Prop. O. .
WO87/06133 10/1987 World Int. Prop. O. .

OTHER PUBLICATIONS

K. Kakemi et al., Yakugaku Zasshi, 81, pp. 1609–14 (1961).
Chemical Abstracts, 56:10142h.
H. Rutner and P. E. Spoerri, J. Org. Chem., 28, pp. 1898–1899 (1963).
R. L. Frank and C. Weatherbee, J. Am. Chem. Soc., 70, pp. 3482–3483 (1948).
N. B. Mahishi et al., J. Indiana Chem. Soc., 42, pp. 67–74 (1965).
M. Ogata and H. Kano, Chem. Pharm. Bull. (TokyoO, 11, p. 32 (1963).

*Primary Examiner*—Cecilia Shen
*Attorney, Agent, or Firm*—William G. Jameson

[57] ABSTRACT

This invention concerns a process for killing internal parasites, especially nematodes, trematodes and cestodes affecting warm blooded animals such as sheep, cattle, swine, goats, dogs, cats, horses and humans as well as poultry by administering an effective amount of a compound of the Formula I.

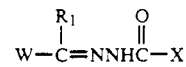

The compounds are readily prepared by conventional chemical reactions.

5 Claims, No Drawings

ANTHELMINTIC ACYLHYDRAZONES, METHOD OF USE AND COMPOSITIONS

CROSS-REFERENCE TO RELATED APPLICATIONS

This application is the national phase of PCT Application PCT/US88/02367, filed July 15, 1988, which is a continuation-in-part of U.S. Ser. No. 07/080,522, filed July 31, 1987, now abandoned.

SUMMARY OF THE INVENTION

This invention pertains to a new method for killing and controlling worms (Helminths), and new formulations for killing and controlling worms in animals, and new chemical compounds. The invention is more particularly directed to a new method for killing and controlling parasitic worms in animals with certain acylhydrazones, to new anthelmintic formulations comprising the same and to new acylhydrazones.

The anthelmintic acylhydrazones have the general structural formula I.

BACKGROUND OF THE INVENTION

The diseases or groups of diseases described generally as helminthiasis are due to infection of the animal with parasitic worms known as helminths. Helminthiasis and helminthosis are prevalent and may lead to serious economic problems in valuable domestic warmblooded animals such as sheep, swine, cattle, goats, dogs, cats, horses, poultry and man. Among the helminths, the groups of worms known as nematodes, trematodes and cestodes cause widespread and often-times serious infections in various species of animals including man. The most common genera of nematodes, trematodes and cestodes infecting the animals referred to above are Dictyocaulus, Haemonchus, Ostertazia Nematodirus, Cooreria, Bunostomum, Oesoohazostomum, Chabertia, Stronzvloides Trichuris, Fasciola, Dicrocoelium, Enterobius, Ascaris, Toxascaris Toxocara, Ascaridia, Caoillaria, Heterakis, Ancvlostoma, Uncinaria Dirofilaria, Onchocerca Taenia, Moniezia, Diovlidium Metastronzvlus, Triodontoohorus, Macracanthorhvnchus, Hvostronzvlus, and Strongylus. Some of these genera attack primarily the intestinal tract while others, inhabit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

The anthelmintic activity of acylhydrazones of formula I has not been previously reported.

The anthelmintic activity of pyridinyl acylhydrazones is disclosed in PCT Application U.S. 86/00072, filed Jan. 23, 1986 and published Aug. 14, 1986 (Case 4199.P); a continuation-in-part of U.S. patent application Ser. No 715,425, filed Mar. 25, 1985 (Case 4199.1); a continuation-in-part of U.S. patent application Ser. No. 700,375, filed Feb. 11, 1985 (Case 4199).

The anthelmintic activity of quinolinyl acylhydrazones is disclosed in PCT Application Ser. No. PCT/US86/00714, filed Apr. 7, 1986, and published Oct. 23, 1986 (Case 4132.P); a continuation-in-part of U.S. patent application Ser. No. 722,104, filed Apr. 11, 1985 (4132).

The anthelmintic activity of quaternaryalkyl acylhydrazones, including pyrazinyl and thiazolyl quaternaryalkyl acylhydrazones, is disclosed in PCT Application U.S. 87/00697, filed Apr. 3, 1987 (Case 4498.P); a continuation-in-part of U.S. patent application Ser. No 849,039, filed Apr. 7, 1986.

The anthelmintic activity of indolinyl, benzofuryl and benzylindolinyl acylhydrazones is disclosed in PCT application Ser. No. PCT/US87/00698, filed Apr. 3, 1987 (Case 4186.P); a continuation-in-part of patent application Ser. No. 849,034, filed Apr. 7, 1986.

The anthelmintic activity of thienyl, furanyl and pyrrolyl acylhydrazones is disclosed in PCT application Ser. No. PCT/US87/00699, filed Apr. 3, 1987 (Case 4237.P); a continuation-in-part of U.S. patent application Ser. No. 849,035, filed Apr. 7, 1986.

DETAILED DESCRIPTION OF THE INVENTION

The acylhydrazones of this invention, including hydrates or pharmaceutically acceptable salts thereof, are represented by Formula I wherein W is selected from the group consisting of
(1) pyrazinyl (A);
(2) pyranyl (B); or
(3) thiazolyl (C);
wherein the variable substituents (1)-(3) are optionally substituted with one or two $C_1$–$C_4$ alkyl, preferably $C_1$–$C_3$ alkyl; $C_1$–$C_3$ alkoxy; $C_1$–$C_3$ alkylthio; halo; trifluoromethyl; or hydroxy; with the proviso that when substituted with two substituents only one substituent is hydroxy;

wherein X is (a) hydrogen; (b) $C_1$–$C_{10}$ alkyl; (c) $C_2$–$C_6$ alkenyl, preferably $C_2$–$C_4$ alkenyl; (d) $C_2$–$C_6$ alkynyl; (e) cyclo($C_3$–$C_{10}$)alkyl optionally substituted with one, 2 or 3 $C_1$–$C_4$ alkyl, or $C_2$–$C_4$ alkenyl; (g) 1-methylpyrrolidinyl; (h) 1-methylpiperidinyl; (i) $C_2$–$C_6$ alkoxyalkyl; (j) cyclo($C_3$–$C_{10}$)alkyl($C_1$–$C_4$)alkyl; (k) phenyl($C_1$–$C_4$)alkyl optionally substituted with one, 2 or 3 $C_1$–$C_4$ alkyl, $C_1$–$C_4$ alkoxy, halo or trifluoromethyl; with the proviso that when X is 3,4-dimethoxyphenylmethyl and W is 2-pyrazinyl, $R_1$ is other than methyl; (l) cyano($C_1$–$C_3$)alkyl; (m) naphthyl($C_1$–$C_3$)alkyl optionally substituted with one or two $C_1$–$C_4$ alkyl, $C_1$–$C_4$ alkoxy, halo, or trifluoromethyl; with the proviso that when X is 1-naphthylmethyl and W is 2-pyrazinyl, $R_1$ is other than methyl; (n) $C_1$–$C_6$ alkoxy, (o) diphenylmethoxy; (p) cyclo($C_3$–$C_6$)alkyloxy optionally substituted with one or two $C_1$–$C_3$ alkyl; (q) phenoxy optionally substituted with one, 2 or 3 $C_1$–$C_4$ alkyl, $C_1$–$C_4$ alkoxy, halo, or trifluoromethyl; (r) benzyloxy optionally substituted with one, 2 or 3 $C_1$–$C_4$ alkyl, $C_1$–$C_4$ alkoxy, halo, or trifluoromethyl; (s) heteroaromatic optionally substituted with one, 2 or 3 $C_1$–$C_4$ alkyl, $C_1$–$C_3$ alkoxy, halo, $C_1$–$C_3$ alkylthio, or trifluoromethyl; (t) phenyl optionally substituted with one, 2 or 3 $C_1$–$C_4$ alkyl, $C_1$–$C_3$ alkoxy, halo, trifluoromethyl, $C_2$–$C_6$ dialkylamino, $C_1$–$C_3$ alkylthio, nitro, or phenoxy optionally substituted with one, 2 or 3 $C_1$–$C_4$ alkyl, $C_1$–$C_3$ alkoxy, halo, or trifluoromethyl; with the proviso that when X is 2-phenoxyphenyl or 2,5-dichlorophenyl and W is 2-pyrazinyl, $R_1$ is other than methyl; (u) phenyl optionally substituted with the divalent $C_1$–$C_2$ alkylenedioxy; (v) naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio, or nitro; (w) bridged polycyclic hydrocarbon substituents of six to 10 nuclear carbons, optionally substituted with one, 2 or 3 ($C_1$–$C_3$) alkyl groups; (x) perhalo(C-

$_1$–C$_7$)alkyl; (y) N-morpholinyl(C$_1$–C$_4$)alkyl; (z) N-piperidinyl(C$_1$–C$_4$)alkyl; (aa) N-pyrrolidinyl(C$_1$–C$_4$)alkyl; and wherein R$_1$ is hydrogen; C$_1$–C$_4$ alkyl; cyclo(C$_3$–C$_6$)alkyl optionally substituted with one, 2 or 3 C$_1$–C$_3$ alkyl, preferably cyclo(C$_3$–C$_5$)alkyl optionally substituted; phenyl optionally substituted with one, 2 or 3 C$_1$–C$_4$ alkyl, halo, trifluoromethyl, or C$_1$–C$_3$ alkoxy; phenyl(C$_1$–C$_3$)alkyl optionally substituted with one, 2 or 3 C$_1$–C$_4$ alkyl, halo, trifluoromethyl, or C$_1$–C$_3$ alkoxy; 1,3-dioxacyclohexan-5-yl; thienylvinyl; furylvinyl; or phenylvinyl.

C_–C_ means the carbon content of various hydrocarbon-containing moieties is indicated by a prefix designating the minimum and maximum number of carbon atoms in the moiety. Thus (C$_1$–C$_3$) alkyl refers to alkyl of one to 3 carbon atoms, inclusive or methyl, ethyl, propyl, and isopropyl.

Halogen atom (halo) refers to a bromo, chloro, iodo or fluoro atom.

Heteroaromatic refers to an aromatic heterocycle of 5 to 10 members, containing one or two heteroatoms selected from the group consisting of oxygen, nitrogen or sulfur and includes quinoline, pyrrole, indole, benzofuran, benzothiophene, quinazoline, quinoxaline, imidazole, pyrazole, oxazole, isoxazole, thiazole, isothiazole, pyridazine, pyrimidine, pyrazine, benzimidazole, benzothiazole, benzoxazole, pyridine, thiophene or furan, as well as the N-oxides, hydrates and pharmaceutically acceptable salts thereof.

Pharmaceutically acceptable refers to those properties and/or substances which are acceptable to the patient from a pharmacologically-toxicological point of view and to the manufacturing pharmaceutical chemist from a physical-chemical point of view regarding composition, formulation, stability, patient acceptance and bioavailability.

Examples of C$_1$–C$_4$ alkyl are methyl, ethyl, propyl, butyl and isomeric forms thereof. Examples of C$_1$–C$_3$ alkoxy are methoxy, ethoxy, propoxy and isomeric forms thereof. Examples of phenoxy substituted with one, 2 or 3 C$_1$–C$_4$ alkyl are (o-, m-, or p-)tolyl, (o-, m-, or p-)ethylphenyl, p-tert-butylphenyl, 2,5-dimethylphenyl, 2,6-dimethylphenyl, 2,4-dimethylphenyl, (2,3,4-, 2,3,5-, 2,3,6-, 2,4,6- or 2,4,5-)trimethylphenyl.

Examples of C$_2$–C$_6$ dialkylamino are dimethylamino, diethylamino, methylethylamino, dipropylamino and ethylpropylamino.

Examples of phenyl(C$_1$–C$_3$)alkyl are benzyl, phenylethyl and phenylpropyl. Examples of phenyl(C$_1$–C$_3$)alky substituted with one, 2 or 3 C$_1$–C$_4$ alkoxy, halo or trifluoromethyl include 4-chlorobenzyl, 2-chlorophenylethyl, p-tolylethyl, 2-methylbenzyl, 4-methoxybenzyl. Examples of C$_1$–C$_3$ alkylthio include methylthio, ethylthio, and n-propylthio.

Examples of substituted cyclo(C$_3$–C$_{10}$)alkyl are chrysanthemyl, 1-methylcyclopropyl and 2-methylcyclopropyl. Examples of cyclo(C$_3$–C$_{10}$)alkyl(C$_1$–C$_4$)alkyl are 2-cyclohexylethyl and cyclohexylmethyl. An example to substituted cyclo(C$_3$–C$_6$)alkyloxy is menthyl.

Examples of naphthyl(C$_1$–C$_3$)alkyl include 2-naphthylmethyl and 1-naphthylethyl. Examples of substituted naphthyl(C$_1$–C$_3$)alkyl is (3,8-dichloro-1-naphthyl)methyl; (4-chloro-1-naphthyl)methyl; and (4-methoxy-1-naphthyl)methyl. Examples of substituted naphthyl include 3,6-dichloro-1-naphthyl; 3,5-dichloro-2-naphthyl; 6-methyl-2-naphthyl; and 4,6-dichloro-1-naphthyl.

Examples of bridged polycyclic hydrocarbon substituents of six to 10 nuclear carbons, optionally substituted with one, 2 or 3 (C$_1$–C$_3$) alkyl groups include exo or endo-2-norbonyl bicyclo[2,2,2]oct-1-yl, and 1-adamantyl.

Examples of perhalo (C$_1$–C$_7$) alkyl include trifluoromethyl, n-heptafluoropropyl and n-undecafluoropentyl.

Preferred acylhydrazones of Formula I are 2-pyrazinyl acylhydrazones (IA), 2-pyranyl acylhydrazones (IB) or 5-thiazolyl acylhydrazones (IC).

Preferred Y and Z of IA, IB and IC include hydrogen, methyl, or a chloro atom.

Preferred R$_1$ includes hydrogen, methyl or ethyl.

Preferred X include hydrogen; C$_1$–C$_4$ alkyl; cyclohexylethyl; phenyl optionally substituted with one, 2 or 3 C$_1$–C$_4$ alkyl, C$_1$–C$_2$ alkoxy, trifluoromethyl and chloro; C$_1$–C$_4$ alkoxy; phenoxy optionally substituted with one, 2 or 3 C$_1$–C$_2$ alkyl, C$_1$–C$_2$ alkoxy, trifluoromethyl and chloro; cyclo(C$_3$–C$_6$)alkyl; pyridinyl; thienyl; furyl; benzyloxy optionally substituted with one or 2 C$_1$–C$_2$ alkoxy; di(C$_1$–C$_2$)alkoxyphenylmethyl; N-morpholinylethyl; or 1-menthyl.

A is pyrazinyl (including pyrazinyl N-oxide and pyrazinyl N,N'-dioxide) optionally substituted with one or two C$_1$–C$_4$ alkyl, preferably C$_1$–C$_3$ alkyl; C$_1$–C$_3$ alkoxy; C$_1$–C$_3$ alkylthio; halo; trifluoromethyl; or hydroxy.

B is pyranyl optionally substituted with one or two C$_1$–C$_4$ alkyl, preferably C$_1$–C$_3$ alkyl; C$_1$–C$_3$ alkoxy; C$_1$–C$_3$ alkylthio; halo; trifluoromethyl; or hydroxy.

C is thiazolyl optionally substituted with one or two C$_1$–C$_4$ alkyl, preferably C$_1$–C$_3$ alkyl; C$_1$–C$_3$ alkoxy; C$_1$–C$_3$ alkylthio; halo; trifluoromethyl; or hydroxy.

Preferred compounds of this invention are the compounds of Table A represented by compound nos.: 1–14, 16–23, 26, 28, 29, 31, 38, 39, 40, 42–45.

Among the acylhydrazones of formula IA:
pyrazinealdehyde isonicotinoylhydrazone; isonicotinic acid (2-pyrazinylmethylene) hydrazide
pyrazinealdehyde nicotinoylhydrazone; nicotinic acid (2-pyrazinylmethylene) hydrazide
pyrazinealdehyde picolinoylhydrazone; picolinic acid (2-pyrazinylmethylene) hydrazide are known See K Kakemi, et al., Yakugaku Zasshi, 81, 1609–14 (1961) or Chemical Abstracts 56:10142h; and H. Rutner and P. E. Spoerri, J. Org Chem, 28 1898–9 (1963).

One embodiment of this invention includes, of course, the anthelmintic use and anthelmintic compositions of compounds of Formula I, IA, IB, or IC hydrates thereof or pharmaceutically acceptable salts thereof.

Still another embodiment of this invention are the novel compounds, hydrates thereof or pharmaceutically acceptable salts thereof according to Formula I, IA, IB, and IC.

The acylhydrazones of this invention (Formula I) are readily prepared by reacting the appropriate ketone (II) with the acylhydrazide/carbazate (III) (Chart A, Scheme A) or by heating the pyridyl ketone (II) with hydrazine (IV) to form the hydrazone intermediate (V) which is then acylated with the halide or anhydride (VI) to form the acylhydrazone (I) (Chart A, Scheme B).

The reaction of Scheme A is carried out in the presence of a suitable solvent, for example, water, alcohols, ethers, halogenated hydrocarbons, hydrocarbons and include methanol, ethanol isopropanol, propanol, hexane, tetrahydrofuran, dioxane, methylene chloride, preferably ethanol. A catalyst such as glacial acetic acid, hydrochloric acid, sulfuric acid or p-toluenesulfonic acid can be utilized to enhance the yield/rate of the reaction, particularly when $R_1$ is alkyl of 3 or more atoms, arylalkyl arylalkenyl or aryl.

The acylation reaction of Scheme B is carried out in the presence of a suitable base such as a tertiary amine, for example, triethylamine or preferably, pyridine. The base may also be the solvent.

The starting compounds are known or can be readily prepared by known methods. R. L. Frank and C. Weatherbee, J. Am. Chem Soc., 70, 3482-3 (1948); N. B. Mahishi, et al., J. Indian Chem. Soc., 42, 67-74 (1965) and M. Ogata and H. Kano, Chem. Pharm. Bull (Tokyo), 11, 32 (1963). The following detailed examples/procedures describe how to prepare various acylhydrazones of the invention and are to be construed as merely illustrative, and not limitations of the preceding disclosure in any way whatsoever. Those skilled in the art will promptly recognize appropriate variations from the procedures both as to reactants as well as to reaction conditions and techniques.

PROCEDURE 1

Preparation of propanoic acid [1-(2-pyrazinyl)ethylidene]hydrazide, Compound 1

A mixture of 6.11 gm (0.05 mole) of 2-acetylpyrazine, 4.41 gm (0.05 mole) of propanoic acid hydrazide and 100 ml of absolute ethanol is refluxed 10 hr. The mixture is cooled. The white crystals which deposit are collected and dried to yield 6.17 gm (64%) of the title compound having a melting point of 181.3° C.

Analysis Calculated: C, 56.24; H, 6 24; N, 29.15; Found: C, 55.89; H, 6.31; N, 29.21.

PROCEDURE 2

Preparation of 2-methylpropanoic acid [1-(2-pyrizinyl)ethylidene]hydrazide, Compound 2

A mixture of 5.49 gm (0.045 mole) of 2-acetylpyrazine, 5.96 gm (0.045 mole) of isobutyric acid hydrazide, 100 ml of absolute ethanol and 1.1 ml of glacial acetic acid is refluxed 24 hr. The reaction mixture is diluted with water to the cloud point. The mixture is cooled. The solid which separates is collected and dried to give 5.07 gm (55%) of the title compound as a white waxey solid having a melting point of 155.7° C.

Analysis Calculated: C, 58.24; H, 6.84; N, 27.1; Found: C, 57.95; H, 6.75; N, 27 13.

PROCEDURE 3

Preparation of butyric acid [1-(6-methyl-2,3-dihydro-2-pyranyl)ethylidene]hydrazide, Compound 33

A mixture of 5.0 gm (0.0356 mole) of 2-acetyl-6-methyl-2,3-dihydropyran, 3.64 gm (0.0356 mole) of n-butyric acid hydrazide and 100 ml of ethanol is refluxed 24 hr. The mixture is diluted with water to the cloud point and chilled. The product is collected, washed with water and dried to give 0.93 gm (12%) of the title compound having a melting point of 72.8° C.

Analysis Calculated: C, 64.26; H, 8.99; N, 12 48; Found: C, 63.98; H, 9.47; N, 12.44.

PROCEDURE 4

Preparation of butyric acid [1-(2,4-dimethyl-5-thiazolyl)ethylidene]hydrazide, Compound 39

A mixture of 5.0 gm (0.0322 mole) of 5-acetyl-2,4-dimethylthiazole, 3.29 gm (0.0322 mole) of butyric acid hydrazide 10 drops of glacial acetic acid and 100 ml of ethanol is refluxed for 48 hr. The reaction mixture is chilled. The product is collected, washed with Skellysolve B and dried to give 1.88 gm (24%) of the title compound having a melting point of 123.7° C.

Analysis Calculated: C, 55.21; H, 7 16; N, 17.55; S, 13.46, Found: C, 55.08; H, 7.39; N, 17 46; S, 13 17.

PROCEDURE 5

Preparation of benzoic acid [1-(2,4-dimethyl-5-thiazolyl)ethylidene]hydrazide, Compound 40

A mixture of 5.0 gm (0.322 mole) of 5-acetyl-2,4-dimethylthiazole, 4.38 gm (0 0322 mole) of benzhydrazide, 10 drops of glacial acid and 100 ml of ethanol is refluxed 48 hrs. The reaction mixture is diluted with water to the cloud point then chilled. The product is collected and dried to give 4.75 gm (54%) of the title compound having a melting point of 138.4° C.

Analysis Calculated: C, 61.57; H, 5.53; N. 15.37; S, 11.73., Found: C, 61.62; H, 5.62; N, 15.54; S, 11.37.

The compounds prepared according to Procedures 1-5 are tabulated in Table A along with other illustrative compounds of the invention prepared following the general procedure indicated (Procedures 1-5) and making non-critical variations, except starting with the appropriate ketone (II) and acylhydrazide/carbazate (III).

The acylhydrazones of this invention (Formula I) are effective against parasitic worms, particularly those of valuable domestic warm-blooded animals and more particularly helminth parasites in ovines (sheep) and bovines (cattle).

Observations in sheep experimentally infected with *Haemonchus contortus* in accordance with Procedure 1, generally confirm. activity at 100 mg/kg of body weight upon oral administration as set forth in Table I. Acylhydrazones which are toxic at 100 mg/kg are expected to exhibit anthelmintic activity at a lower nontoxic dose.

PROCEDURE NO. 1

In individual experiments all sheep are treated identically, however non-critical variations occur between experiments. All of the sheep used in this procedure are treated twice with levamisole hydrochloride orally at 8 mg/kg or once each with ivermectin parenterally at 200 μg/kg and levamisole hydrochloride orally at 8 mg/kg. The second treatment in each case is administered 4-7 days after the first treatment. Two weeks after the second treatment all sheep are inoculated per os with ~3,500 to ~7,500 infective larvae of *H. contortus*. Rectal fecal samples are taken from each sheep 26-41 days post-inoculation (PI), and these samples are examined for eggs of *H. contortus* using the McMaster counting chamber technique. All sheep harboring good infections of *H. contortus* are randomly allocated to a treatment group; those which do not exhibit suitable infections are dropped from the study. One-three days later on days 27-42 PI each sheep remaining in the study (excluding the nontreated controls) is treated with a test compound (orally at 100 mg/kg unless indicated otherwise) or a standard (levamisole hydrochloride orally at 8 mg/kg) or is used as an untreated control. All sheep received food and water ad lib. throughout the experiment.

Prior to administration, all solid compounds are finely ground using a mortar and pestle. The compounds are suspended in 20-30 ml of sterile vehicle TM 98 (each ml contains: carboxymethylcellulose—10 mg. polysorbate 80—4mg. propylparaben—0.42 mg) using a sonicator and administered along with a tap water wash via a stomach tube. All test compounds are given to a single sheep/route of administration. Two or more sheep are treated with levamisole hydrochloride and five are used as nontreated controls. All animals are monitored for signs of toxicity following treatment.

The sheep are sacrificed 7-12 days after treatment (days 35-49 PI), and the abomasum is ligated and removed from each sheep. Each abomasum is longitudinally sectioned and rinsed into an 80 mesh sieve. Sieve contents are collected in individual containers and fixed in formol-alcohol. Later each sample is transferred to a 1000 or 2000 ml beaker and the volume brought to 400-1000 ml with tap water. The total number of worms in a 40-100 ml aliquot (10%) is determined. When no worms are found in the 10% aliquot, the entire sample is examined. Total worm number/sheep and percentage clearance for each treatment are calculated. Percentage clearance for a particular test compound in a given trial is determined according to the following formula:

Percentage Clearance (Test Compound) = [(Mean number of worms recovered from nontreated control sheep Number of worms recovered from treated sheep)/Mean number of worms recovered from nontreated control sheep] × 100.

Sheep which die within 24 hr following treatment are not examined for worms, while any that die between 24 hr post-treatment and necropsy are examined in an identical manner as that described above. The results of various trials are combined and reported in Table I as percentage clearance.

DETAILED DESCRIPTION (cont'd)

The acylhydrazones of Formula I can be used as the pure compounds or as mixtures of pure compounds but for practical reasons the compounds are preferably formulated as anthelmintic compositions and administered as a single or multiple dose, alone or in combination with other anthelmintics (e.g. avermectins, benzimid azoles, levamisole, praziquantel, etc.). For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity. In addition, the active compound(s) can be administered topically to the animal in a conventional pour-on formulation.

Pure compounds, mixtures of the active compounds, or combinations thereof with a solid carrier can be administered in the animal's food, or administered in the form of tablets, pills, boluses, wafers, pastes, and other conventional unit dosage forms, as well as sustained release dosage forms which deliver the active compound over an extended period of days, weeks or months. All of these various forms of the active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal feed to about 90 or 95 percent or more in a pill or capsule. In the latter form, one might use no more carrier than sufficient to bind the particles of active compound.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg per kg body weight for each 100 lb pig in its daily ration.

A solid diluent carrier need not be a homogeneous entity, but mixtures of different diluent carriers can include small proportions of adjuvants such as water; alcohols; protein solutions and suspensions like skimmed milk; edible oils, solutions e.g., syrups; and organic adjuvants such as propylene glycols, sorbitol glycerol diethyl carbonate, and the like.

The solid carrier formulations of the inventions are conveniently prepared in unit dosage forms to facilitate administration to animals. Accordingly, several large boluses (about 20 g weight) amounting to about 54 g of active compound would be required for a single dosage to a 900 lb horse at a dosage rate of 50 mg/kg of body weight. Similarly, a 60 lb lamb at a dosage rate of 100 mg/kg of body weight would require a pill capsule, or bolus containing about 2.7 g of active compound. A small dog, on the other hand, weighing about 20 lbs. would require a total dosage of about 225 mg at a dosage rate of 25 mg/kg of body weight. The solid, unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or proplrylactic levels of the active compound. At present, it is known that a dose of 100 mg/kg of body weight in sheep of an acylhydrazone of this invention will effectively combat a wide variety of parasites. Much lower effective dosages of various compounds are contemplated, e.g., in the range of 1 to 75 mg/kg of body weight.

In other animals, and for other kinds of parasitic worms, definitive dosages can be proposed. Contemplated are dosage rates of about 1 mg to about 800 mg/kg of body weight. A preferred, contemplated range of dosage rates is from about 5 mg to about 400 mg/kg of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protracted delivery formulation) so as to provide therapeutic and/or prophylactic dosage amounts over an extended period. Unit dosage forms in accordance with this invention can have anywhere from less than 1 mg to 500 g of active compound per unit.

Although the anthelmintic agents of this invention will find their primary use in the treatment and/or prevention of helminth parasitisms in valuable warm-blooded domesticated animals such as sheep, cattle, horses, dogs, swine, goats and poultry, they are also effective in treatment that occurs in other warm blooded animals including man. The optimum amount to be employed for best results will, of course, depend upon the particular compound employed. species of animal to be treated, the regimen of treatment and the type and severity of helminth infection. Generally good results are obtained with compounds of Formula I by the oral or parenteral route of administration of about 1 to 300 mg/kg of animal bodyweight (such total dose being given at one time, in a protracted manner or in divided doses over a short period of time such as 1–4 days). The technique for administering these materials to animals are known to those skilled in the veterinary and medical fields.

It is contemplated that the acylhydrazones of Formula I can be used to treat various helminth diseases in humans, including those caused by Ascaris, Enterobius, Ancylostoma, Trichuris, Strongyloides, Fasciola, Taenia, and/or Onchocerca or other filariae at a dose of from 1 mg/kg to 300 mg/kg of body weight upon oral and/or parenteral administration.

DEFINITIONS

The definitions and explanations below are for the terms as used throughout the entire patent application including both the specification and claims.

All temperatures are in degrees Celsius.

TLC refers to thin-layer chromatography.

Brine refers to an aqueous saturated sodium chloride solution.

When solvent pairs are used. the ratio of solvents used are volume/volume (v/v).

TABLE A

| C | W | $R_1$ | X | m.p. (°C.) | P | H |
|---|---|---|---|---|---|---|
| 1 | 2-pyrazinyl | $CH_3$ | $CH_3CH_2$ | 181.3 | 1 | — |
| 2 | 2-pyrazinyl | $CH_3$ | $i-C_3H_7$ | 155.7 | 2 | — |
| 3 | 2-pyrazinyl | $CH_3$ | $C_3H_7$ | 166.7 | 1 | — |
| 4 | 2-pyrazinyl | $CH_3$ | $4-CH_3CH_2OPh$ | 166.7 | 1 | — |
| 5 | 2-pyrazinyl | $CH_3$ | Ph | 183.8 | 1 | — |
| 6 | 2-pyrazinyl | $CH_3$ | $CH_3CH_2O$ | 179.7 | 1 | — |
| 7 | 3-methyl-2-pyrazinyl | $CH_3$ | $CH_3CH_2$ | 145.1 | 1 | — |
| 8 | 3-methyl-2-pyrazinyl | $CH_3$ | $CH_3CH_2CH_2$ | 118.1 | 1 | — |
| 9 | 3-methyl-2-pyrazinyl | $CH_3$ | $i-C_3H_7$ | 110.7 | 2 | — |
| 10 | 3-methyl-2-pyrazinyl | $CH_3$ | $4-CH_3CH_2OPh$ | 121.4 | 2 | + |
| 11 | 3-methyl-2-pyrazinyl | $CH_3$ | Ph | 123.4 | 2 | — |
| 12 | 3-methyl-2-pyrazinyl | $CH_3$ | $CH_3CH_2O$ | 138.3 | 2 | — |
| 13 | 3-ethyl-2-pyrazinyl | $CH_3$ | $CH_3CH_2CH_2$ | 80.6 | 2 | — |
| 14 | 3-ethyl-2-pyrazinyl | $CH_3$ | $i-C_3H_7$ | 105.4 | 2 | — |
| 15 | 3-ethyl-2-pyrazinyl | $CH_3$ | $4-CH_3CH_2OPh$ | 163.5 | 2 | — |
| 16 | 3-ethyl-2-pyrazinyl | $CH_3$ | Ph | 139.6 | 2 | — |
| 17 | 3-ethyl-2-pyrazinyl | $CH_3$ | $CH_3CH_2O$ | 75.6 | 2 | — |
| 18 | 2-pyrazinyl | $CH_3$ | $c-C_6H_{11}$ | 181.6 | 1 | — |
| 19 | 2-pyrazinyl | $CH_3$ | $c-C_6H_{11}CH_2$ | 134.6 | 1 | — |
| 20 | 2-pyrazinyl | $CH_3$ | $c-C_6H_{11}CH_2CH_2$ | 127.5 | 1 | — |
| 21 | 2-pyrazinyl | $CH_3$ | 3-pyridyl | 201.2 | 1 | — |
| 22 | 2-pyrazinyl | $CH_3$ | 4-pyridyl | 210.6 | 1 | — |
| 23 | 2-pyrazinyl | $CH_3$ | $PhCH_2$ | 176.8 | 1 | — |
| 24 | 2-pyrazinyl | $CH_3$ | 2-PhOPh | 207.2 | 1 | — |
| 25 | 2-pyrazinyl | $CH_3$ | $3,4-(CH_3O)_2PhCH_2$ | 207.7 | 1 | — |
| 26 | 2-pyrazinyl | $CH_3$ | $4-CH_3OPh$ | 180.6 | 1 | — |
| 27 | 2-pyrazinyl | $CH_3$ | $c-C_3H_5$ | 207.1 | 1 | — |
| 28 | 2-pyrazinyl | $CH_3$ | $PhCH_2O$ | 142.1 | 1 | — |
| 29 | 2-pyrazinyl | $CH_3$ | $4-CH_3Ph$ | 194.5 | 1 | — |
| 30 | 2-pyrazinyl | $CH_3$ | $2,5-(Cl)_2Ph$ | 177.1 | 1 | — |
| 31 | 2-pyrazinyl | $CH_3$ | $4-CH_3OPhCH_2O$ | 212.1 | 1 | — |
| 32 | 2-pyrazinyl | $CH_3$ | 1-naphthyl$CH_2$ | 200.5 | 1 | — |

TABLE A-continued

| C | W | $R_1$ | X | m.p. (°C.) | P | H |
|---|---|---|---|---|---|---|
| 33 | 6-methyl-2,3-dihydro-2-pyranyl | $CH_3$ | $n-C_3H_7$ | 72.8 | 3 | — |
| 34 | 6-methyl-2,3-dihydro-2-pyranyl | $CH_3$ | $CH_3CH_2O$ | 122.2 | 3 | — |
| 35 | 6-methyl-2,3-dihydro-2-pyranyl | $CH_3$ | Ph | 103.3 | 3 | + |
| 36 | 6-methyl-2,3-dihydro-2-pyranyl | $CH_3$ | 4-pyridyl | 131.2 | 3 | — |
| 37 | 6-methyl-2,3-dihydro-2-pyranyl | $CH_3$ | $c-C_6H_{11}$ | 73.7 | 3 | + |
| 38 | 6-methyl-2,3-dihydro-2-pyranyl | $CH_3$ | $PhCH_2O$ | 110.3 | 3 | — |
| 39 | 2,4-dimethyl-5-thiazolyl | $CH_3$ | $n-C_3H_7$ | 123.7 | 4 | — |
| 40 | 2,4-dimethyl-5-thiazolyl | $CH_3$ | Ph | 138.4 | 5 | — |
| 41 | 2,4-dimethyl-5-thiazolyl | $CH_3$ | $c-C_6H_{11}$ | 161.9 | 4 | — |
| 42 | 2,4-dimethyl-5-thiazolyl | $CH_3$ | $CH_2CH_3$ | 143.7 | 4 | — |
| 43 | 2,4-dimethyl-5-thiazolyl | $CH_3$ | $c-C_6H_{11}CH_2CH_2$ | 128.3 | 4 | — |
| 44 | 2,4-dimethyl-5-thiazolyl | $CH_3$ | $PhCH_2O$ | 139.2 | 4 | — |
| 45 | 2,4-dimethyl-5-thiazolyl | $CH_3$ | $CH_3CH_2O$ | 98.0 | 5 | — |

TABLE I

| Compound # | H. contortus % clearance PO |
|---|---|
| 1 | 99.6 |
| 2 | 99.6 |
| 3 | 99.9 |
| 4 | 94.3 |
| 5 | 100 |
| 6 | 100 |
| 7 | 99.6 |
| 8 | 99.2 |
| 9 | 100 |
| 10 | 99.2 |
| 11 | 81.2 |
| 12 | 100 |
| 13 | 90.2 |
| 14 | 98.8 |
| 15 | 50.9 |
| 16 | 99.2 |
| 17 | 99.8 |
| 18 | 100 |
| 19 | 100 |
| 20 | 82.4 |
| 21 | 99.6 |
| 22 | 99.6 |
| 23 | 83.6 |
| 24 | 0 |
| 25 | 0 |
| 26 | 98.4 |
| 27 | toxic |
| 28 | 100 |
| 29 | 100 |
| 30 | 0 |
| 31 | 98.9 |
| 32 | 0 |
| 33 | 43.2* |
| 34 | 77.3 |
| 35 | N.T. |
| 36 | 70.4 |
| 37 | N.T. |
| 38 | 96.3 |
| 39 | 100** |
| 40 | 99.7 |
| 41 | N.T. |
| 42 | 100 |
| 43 | 100 |
| 44 | 99.2 |
| 45 | 99.7 |

*Dosed at 34 mg/kg
**Dosed at 55.6 mg/kg

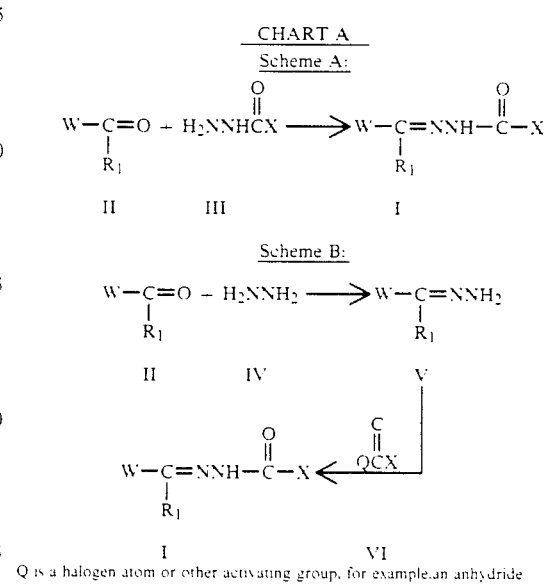

CHART A

Scheme A:

Scheme B:

Q is a halogen atom or other activating group, for example, an anhydride

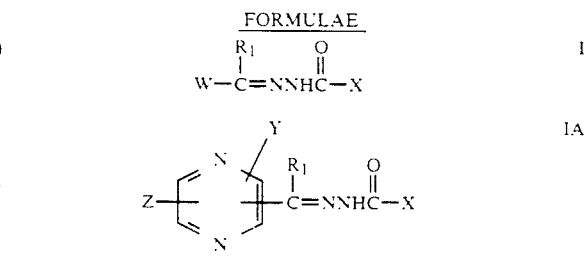

FORMULAE

-continued
FORMULAE

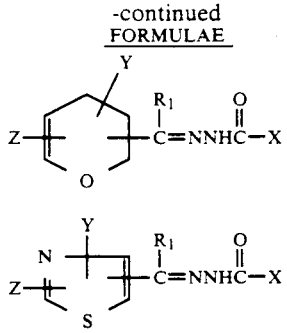

We claim:
1. A compound, hydrate thereof or pharmaceutical acceptable salt thereof of the formula

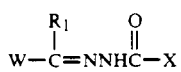

wherein W is selected from the group consisting of
(1) pyrazinyl (A);
(2) pyranyl (B); or
(3) thiazolyl (C);
wherein the variable substituents (1)-(3) are optionally substituted with one or two $C_1$-$C_4$ alkyl; $C_1$-$C_3$ alkoxy; $C_1$-$C_3$ alkylthio; halo; trifluoromethyl; or hydroxy; with the proviso that when substituted with two substituents only one substituent is hydroxy;
wherein X is (a) hydrogen; (b) $C_1$-$C_{10}$ alkyl; (c) $C_2$-$C_6$ alkenyl; (d) $C_2$-$C_6$ alkynyl; (e) cyclo($C_3$-$C_{10}$)alkyl optionally substituted with one, 2 or 3 $C_1$-$C_4$ alkyl, or $C_2$-$C_4$ alkenyl, (f) 1-methylpyrrolidinyl; (g) 1-methylpiperidinyl; (h) $C_2$-$C_6$ alkoxyalkyl; (i) cyclo($C_3$-$C_{10}$)alkyl($C_1$-$C_4$)alkyl; (j) phenyl($C_1$-$C_4$)alkyl optionally substituted with one, 2 or 3 $C_1$-$C_4$ alkyl, $C_1$-$C_4$ alkoxy, halo, or trifluoromethyl; with the proviso that when X is 3,4-dimethoxyphenylmethyl and W is 2-pyrazinyl, $R_1$ is other than methyl; (k) cyano($C_1$-$C_3$)alkyl; (l) naphthyl($C_1$-$C_3$)alkyl optionally substituted with one or two $C_1$-$C_4$ alkyl, $C_1$-$C_4$ alkoxy, halo, or trifluoromethyl; with the proviso than when X is 1-naphthylmethyl and W is 2-pyrazinyl, $R_1$ is other than methyl; (m) $C_1$-$C_6$ alkoxy; (n) diphenylmethoxy; (o) cyclo($C_3$-$C_6$)alkyloxy optionally substituted with one or two $C_1$-$C_3$ alkyl; (p) phenoxy optionally substituted with one, 2 or 3 $C_1$-$C_4$ alkyl, $C_1$-$C_4$ alkoxy, halo, or trifluoromethyl; (q) benzyloxy optionally substituted with one, 2 or 3 $C_1$-$C_4$ alkyl, $C_1$-$C_4$ alkoxy, halo, or trifluoromethyl; (r) heteroaromatic of 5 to 10 members, containing one or two heteroatoms selected from the group consisting of oxygen, nitrogen or sulfur, and optionally substituted with one, 2 or 3 $C_1$-$C_4$ alkyl, $C_1$-$C_3$ alkoxy, halo, $C_1$-$C_3$ alkylthio, or trifluoromethyl; (s) phenyl optionally substituted with one, 2 or 3 $C_1$-$C_4$ alkyl, $C_1$-$C_3$ alkoxy, halo, trifluoromethyl, $C_2$-k$C_6$ dialkylamino, $C_1$-$C_3$ alkylthio, nitro, or phenoxy optionally substituted with one, 2 or 3 $C_1$-$C_4$ alkyl, $C_1$-$C_3$ alkoxy, halo, or trifluoromethyl; with the proviso that when X is 2-phenoxyphenyl or 2,5-dichlorophenyl and W is 2-pyrazinyl, $R_1$ is other than methyl; (t) phenyl optionally substituted with the divalent $C_1$-$C_2$ alkylenedioxy; (u) naphthyl optionally substituted with one or 2 $C_1$-$C_4$ alkyl, $C_1$-$C_3$ alkoxy, halo, trifluoromethyl, $C_2$-$C_6$ dialkylamino, $C_1$-$C_3$ alkylthio, or nitro; (v) bridged polycyclic hydrocarbon substituents selected from the group consisting of exo or endo-2-norbonyl, bicyclo[2,2,2]-oct-1-yl, and 1-adamantyl; (w) perhalo ($C_1$-$C_7$)alkyl; (x) N-morpholinyl($c_1$-$C_4$)alkyl; (y) N-piperidinyl(-$C_1$-$C_4$)alkyl; (z) N-pyrrolidinyl($C_1$-$C_4$)alkyl; and
wherein $R_1$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy; 1,3-dioxacyclohexan-5-yl; theinylvinyl; furylvinyl; or phenylvinyl;
other than
isonicotinic acid (2-pyrazinylmethylene) hydrazide;
nicotinic acid (2-pyrazinylmethylene) hydrazide; or
picolinic acid (2-pyrazinylmethylene) hydrazide.
2. A compound according to claim 1 wherein W is pyrazinyl and the compound, hydrate, pharmaceutically acceptable acid addition salt, N-oxide, or N,N'-dioxide thereof is a pyrazinyl acylhydrazone (IA).
3. A compound according to claim 2 wherein (s) is selected from quinoline, pyrrole, indole, benzofuran, benzothiophene, quinazoline, quinoxaline, imidazole, pyrazole, oxazole, isoxazole, thiazole, isothiazole, pyridazine, pyrimidine, pyrazine, benzimidazole, benzothiazole, benzoxazole, pyridine, thiophene or furan, optionally substituted with one, 2 or 3 $C_1$-$C_4$ alkyl, $C_1$-$C_3$ alkoxy, halo, $C_1$-$C_3$ alkylthio, or trifluoromethyl.
4. The compound according to claim 2 wherein the compound or hydrate thereof is selected from the group consisting of
propanoic acid [1-(2-pyrazinyl)ethylidene]hydrazide (Cpd #1);
2-methylpropanoic acid [1-(2-pyrazinyl)ethylidene]-hydrazide (Cpd #2);
butyric acid [1-(2-pyrazinyl)ethylidene]hydrazide (Cpd #3);
4-ethoxybenzoic acid [1-(2-pyrazinyl)ethylidene]hydrazide (Cpd #4);
benzoic acid [1-(2-pyrazinyl)ethylidene]hydrazide (Cpd #5);
ethyl [1-(2-pyrazinyl)ethylidene]carbazate (Cpd #6);
propanoic acid [1-(3-methyl-2-pyrazinyl)ethylidene]-hydrazide (Cpd #7);
butyric acid [1-(3-methyl-2-pyrazinyl)ethylidene]hydrazide (Cpd #8);
2-methylpropanoic acid [1-(3-methyl-2-pyrazinyl)ethylidene]hydrazide (Cpd #9);
4-ethoxybenzoic acid [1-(3-methyl-2-pyrazinyl)ethylidene]hydrazide (Cpd #10);
benzoic acid [1-(3-methyl-2-pyrazinyl)ethylidene]hydrazide (Cpd #11);
ethyl [1-(3-methyl-2-pyrazinyl)ethylidene]carbazate (Cpd #12);
butyric acid [1-(3-ethyl-2-pyrazinyl)ethylidene]hydrazide (Cpd #13);
2-methylpropanoic acid [1-(3-ethyl-2-pyrazinyl)ethylidene]hydrazide (Cpd #14);
benzoic acid [1-(3-ethyl-2-pyrazinyl)ethylidene]hydrazide (Cpd #16);
ethyl [1-(3-ethyl-2-pyrazinyl)ethylidene]carbazate (Cpd #17);

cyclohexanecarboxylic acid [1-(2-pyrazinyl)ethylidene]hydrazide (Cpd #18);
2-cyclohexylethanoic acid [1-(2-pyrazinyl)ethylidene]hydrazide (Cpd #19);
3-cyclohexylpropanoic acid [1-(2-pyrazinyl)ethylidene]hydrazide (Cpd #20);
nicotinic acid [1-(2-pyrazinyl)ethylidene]hydrazide (Cpd #21);
isonicotinic acid [1-(2-pyrazinyl)ethylidene]hydrazide (Cpd #22);
2-phenylethanoic acid [1-(2-pyrazinyl)ethylidene]hydrazide (Cpd #23);
4-methoxybenzoic acid [1-(2-pyrazinyl)ethylidene]hydrazide (Cpd #26);
benzyl [1-(2-pyrazinyl)ethylidene]carbazate (Cpd #28);
4-methylbenzoic acid [1-(2-pyrazinyl)ethylidene]hydrazide (Cpd #29); or
4-methoxybenzyl [1-(2-pyrazinyl)ethylidene]carbazate (Cpd #31).
benzyl [1-(6-methyl-2,3-dihydro-2-pyranyl)ethylidene]carbazate (Cpd #38);
butyric acid [1-(2,4-dimethyl-5-thiazolyl)ethylidene]hydrazide (Cpd #39);
benzoic acid [1-(2,4-dimethyl-5-thiazolyl)ethylidene]hydrazide (Cpd #40);
propanoic acid [1-(2,4-dimethyl-5-thiazolyl)ethylidene]hydrazide (Cpd #42);
3-cyclohexylpropanoic acid [1-(2,4-dimethyl-5-thiazolyl)ethylidene]hydrazide (Cpd #43);
benzyl [1-(2,4-dimethyl-5-thiazolyl)ethylidene]carbazate (Cpd #44); or
ethyl [1-(2,4-dimethyl-5-thiazolyl)ethylidene]carbazate (Cpd #45).

5. An anthelmintic composition for administration to animals comprising a physiologically acceptable carrier and adjuvants, and at least an effective anthelmintic amount of an acylhydrazone, hydrate thereof or pharmaceutically acceptable salt thereof of the formula:

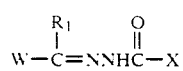

I wherein W is selected from the group consisting of
(1) pyrazinyl (A);
(2) pyranyl (B); or,
(3) thiazolyl (C);
wherein the variable substituents (1)-(3) are optionally substituted with one or two $C_1-C_4$ alkyl; $C_1-C_3$ alkoxy; $C_1-C_3$ alkylthio; halo; trifluoromethyl; or hydroxy; with the proviso that when substituted with two substituents only one substituent is hydroxy;
wherein X is (a) hydrogen; (b) $C_1-C_{10}$ alkyl; (c) $C_2-C_6$ alkenyl; (d) $C_2-C_6$ alkynyl; (e) cyclo($C_3-C_{10}$)alkyl optionally substituted with one, 2 or 3 $C_1-C_4$ alkyl, or $C_2-C_4$ alkenyl; (f) 1-methylpyrrolidinyl; (g) 1-methylpiperidinyl; (h) $C_2-C_6$ alkoxyalkyl; (i) cyclo($C_3-C_{10}$)alkyl($C_1-C_4$)alkyl; (j) phenyl($C_1-C_4$)alkyl optionally substituted with one, 2 or 3 $C_1-C_4$ alkyl, $C_1-C_4$ alkoxy, halo, or trifluoromethyl; with the proviso that when X is 3,4-dimethoxyphenylmethyl and W is 2-pyrazinyl, $R_1$ is other than methyl; (k) cyano($C_1-C_3$)alkyl; (l) naphthyl($C_1-C_3$)alkyl optionally substituted with one or two $C_1-C_4$ alkyl, $C_1-C_4$ alkoxy, halo, or trifluloromethyl; with the proviso that when X is 1-naphthylmethyl and W is 2-pyrazinyl, $R_1$ is other than methyl; (m) $C_1-C_6$ alkoxy; (n) diphenylmethoxy; (o) cyclo($C_3-C_6$)alkyloxy optionally substituted with one or two $C_1-C_3$ alkyl; (p) phenoxy optionally substituted with one, 2 or 3 $C_1-C_4$ alkyl, $C_1-C_4$ alkoxy, halo, or trifluoromethyl; (q) benzyloxy optionally substituted with one, 2 or 3 $C_1-C_4$ alkyl, $C_1-C_4$ alkoxy, halo, or trifluoromethyl; (r) heteroaromatic of 5 to 10 members, containing one or two heteroatoms selected from the group consisting of oxygen, nitrogen or sulfur, and optionally substituted with one, 2 to 3 $C_1-C_4$ alkyl, $C_1-C_3$ alkoxy, halo, $C_1-C_3$ alkylthio, or trifluoromethyl; (s) phenyl optionally substituted with one, 2 or 3 $C_1-C_4$ alkyl, $C_1-C_3$ alkoxy, halo, trifluoromethyl, $C_2-C_6$ dialkylamino, $C_1-C_3$ alkylthio, nitro, or phenoxy optionally substituted with one, 2 or 3 $C_1-C_4$ alkyl, $C_1-C_3$ alkoxy, halo, or trifluoromethyl; with the proviso that when X is 2-phenoxyphenyl or 2,5-dichlorophenyl and W is 2-pyrazinyl, $R_1$ is other than methyl; (t) phenyl optionally substituted with the divalent $C_1-C_2$ alkylenedioxy; (u) naphthyl optionally substituted with one or $2C_1-C_4$ alkyl, $C_1-C_3$ alkoxy, halo, trifluoromethyl, $C_2-C_6$ dialkylamino, $C_1-C_3$ alkylthio, or nitro; (v) bridged polycylic hydrocarbon substituents selected from the group consisting of exo or endo-2-norbonyl, bicyclo[2,2,2]-oct-1-yl, and 1-adamantyl; (w) perhalo($C_1-C_7$)alkyl; (x) N-morpholinyl($C_1-C_4$)alkyl; (y) N-piperidinyl($C_1-C_4$)alkyl; (z) N-pyrrolidinyl($C_1-C_4$)alkyl; and
wherein $R_1$ is hydrogen; $C_1-C_4$ alkyl; cyclo($C_3-C_6$)alkyl optionally substituted with one, 2 or 3 $C_1-C_3$ alkyl; phenyl optionally substituted with one, 2 or 3 $C_1-C_4$ alkyl, halo, trifluoromethyl, or $C_1-C_3$ alkoxy; phenyl($C_1-C_3$)alkyl optionally substituted with one, 2 or 3 $C_1-C_4$ alkyl, halo, trifluoromethyl, or $C_1-C_3$ alkoxy; 1,3-dioxacyclohexan-5-yl; thienylvinyl; furylvinyl; or phenylvinyl;
other than
isonicotinic acid (2-pyrazinylmethylene) hydrazide;
nicotinic acid (2-pyrazinylmethylene) hydrazide; or
picolinic acid (2-pyrazinylmethylene) hydrazide.

* * * * *